United States Patent
Ohno et al.

(10) Patent No.: US 7,084,316 B2
(45) Date of Patent: Aug. 1, 2006

(54) PROCESS FOR PURIFYING PENTAFLUOROETHANE, PROCESS FOR PRODUCING THE SAME, AND USE THEREOF

(75) Inventors: Hiromoto Ohno, Kawasaki (JP); Toshio Ohi, Tokyo (JP)

(73) Assignee: Showa Denko K.K., Tokyo (JP)

( * ) Notice: Subject to any disclaimer, the term of this patent is extended or adjusted under 35 U.S.C. 154(b) by 0 days.

(21) Appl. No.: 10/488,288

(22) PCT Filed: Jun. 30, 2003

(86) PCT No.: PCT/JP03/08295

§ 371 (c)(1), (2), (4) Date: Mar. 2, 2004

(87) PCT Pub. No.: WO2004/005226

PCT Pub. Date: Jan. 15, 2004

(65) Prior Publication Data

US 2005/0124834 A1    Jun. 9, 2005

Related U.S. Application Data

(60) Provisional application No. 60/394,267, filed on Jul. 9, 2002.

(30) Foreign Application Priority Data

Jul. 2, 2002    (JP)    ............... 2002-192960

(51) Int. Cl.
  *C07C 17/38* (2006.01)
  *C07C 17/00* (2006.01)
  *C07C 17/20* (2006.01)

(52) U.S. Cl. .................. 570/177; 570/123; 570/164; 570/170; 570/179

(58) Field of Classification Search ................ 570/101, 570/123, 164, 170, 177, 179
See application file for complete search history.

(56) References Cited

U.S. PATENT DOCUMENTS

| 3,026,350 A | * | 3/1962 | Warolin et al. ............. 560/138 |
| 3,026,359 A | * | 3/1962 | Mastrangelo et al. ....... 570/179 |
| 5,453,551 A |   | 9/1995 | Lacroix et al. |
| 6,274,782 B1 | * | 8/2001 | Ohno et al. .................. 570/179 |
| 2003/0034309 A1 | * | 2/2003 | Ohno et al. .................. 210/690 |

FOREIGN PATENT DOCUMENTS

| EP | 0 844 226 | 5/1998 |
| WO | WO 94 22793 A | 10/1994 |
| WO | WO 01 83412 A | 11/2001 |

OTHER PUBLICATIONS

Matsumoto et al., Purification of pentafluoroethane, Chemical Abstract CAPLUS Document No. 121:82494, (JP 06092879),. 1994.*

Communication from foreign patent office dated Sep. 27, 2005.

* cited by examiner

*Primary Examiner*—J. Parsa
(74) *Attorney, Agent, or Firm*—Sughrue Mion, PLLC

(57) ABSTRACT

A process comprising bringing crude pentafluoroethane containing at least one compound selected from the group consisting of hydrofluorocarbons containing one carbon atom, hydrochlorofluorocarbons containing one carbon atom and hydrochlorocarbons containing one carbon atom, into contact with an adsorbent comprising a zeolite having an average pore size of 3 to 6 Å and a silica/aluminum ratio of 2.0 or less and/or a carbonaceous adsorbent having an average pore size of 3.5 to 6 Å, to reduce the content of the compound. The purified gas can be used as a low temperature refrigerant or an etching gas.

12 Claims, No Drawings

PROCESS FOR PURIFYING PENTAFLUOROETHANE, PROCESS FOR PRODUCING THE SAME, AND USE THEREOF

CROSS-REFERENCE TO RELATED APPLICATION

This application is an application filed under 35 U.S.C. §111(a) claiming benefit pursuant to 35 U.S.C. §119(e)(1) of the filing date of the Provisional Application 60/394,267 filed Jul. 9, 2002, pursuant to 35 U.S.C. §111(b).

TECHNICAL FIELD

The present invention relates to a purification process, a production process and uses of pentafluoroethane.

BACKGROUND ART

Pentafluoroethane ($CF_3CHF_2$) is used, as examples, as a low temperature refrigerant or an etching gas and is also used as a starting material for the production of hexafluoroethane ($CF_3CF_3$).

For the production of pentafluoroethane, the following methods have heretofore been known, as examples, (1) a method of fluorinating tetrachloroethylene ($CCl_2=CCl_2$) or a fluoride thereof with hydrogen fluoride (see, Japanese Unexamined Patent Publication No. 8-268932 (JP-A-8-268932)), (2) a method of reducing and hydrogenating chloropentafluoroethane ($CF_3CClF_2$) (see, Japanese Patent No. 2540409), and (3) a method of reacting a fluorine gas with a halogen-containing ethylene (see, Japanese Unexamined Patent Publication No. 1-38034 (JP-A-1-38034)).

The pentafluoroethanes produced by these methods contain various impurities such as hydrochlorocarbons (HCC), chlorofluorocarbons (CFC), hydrochlorofluorocarbons (HCFC) and hydrofluorocarbons (HFC).

In order to obtain high-purity pentafluoroethane, these impurities must be removed as much as possible. Among these impurities, various purification methods have been proposed to remove chlorofluorocarbons not only for attaining high purity but also for preventing the depletion of the ozone layer. Chloropentafluoroethane is a compound having a boiling point close to that of pentafluoroethane and difficult to separate by ordinary distillation, however, for example, the following purification methods may be used therefor:

(1) a method by extractive distillation (see, Japanese International Application Domestic Publication No. 9-508626 (JP-A-9-508626)), (2) a method of reducing and hydrogenating chloropentafluoroethane (see, Japanese Unexamined Patent Publication No. 8-301801 (JP-A-8-301801)), (3) a method of removing chloropentafluoroethane after fluorinating it with hydrogen fluoride (HF) (see, Japanese Unexamined Patent Publication No. 2001-48816 (JP-A-2001-48816)), and (4) a method of removing chloropentafluoroethane after adsorbing it by using an adsorbent (see, Japanese Unexamined Patent Publication No. 6-92879 (JP-A-6-92879)).

Chloromethane ($CH_3Cl$), which is one of hydrochlorocarbons, forms an azeotropic mixture or azeotrope-like mixture with pentafluoroethane and this compound is very difficult to separate from the pentafluoroethane. Furthermore, difluoromethane ($CH_2F_2$) and 1,1,1-trifluoroethane ($CF_3CH_3$), which are hydrofluorocarbons, each form an azeotropic mixture or azeotrope-like mixture with pentafluoroethane and these compounds are very difficult to separate from the pentafluoroethane.

As for the method of purifying and thereby removing impurities comprising these difficult-to-separate hydrochlorocarbons or hydrofluorocarbons, for example, a purification method by extractive distillation and a purification method of removing these impurities by the adsorption using an activated carbon are known. However, the purification method by extractive distillation has a problem that a plurality of expensive facilities such as distillation tower are necessary and the equipment cost rises highly. Also, the purification method by the adsorption using an activated carbon cannot provide a sufficient effect.

DISCLOSURE OF INVENTION

Under these circumstances, an object of the present invention is to provide an industrially advantageous purification process to obtain high-purity pentafluoroethane which can be used as a low temperature refrigerant or an etching gas. Another object of the present invention is to provide a production process and uses of pentafluoroethane.

As a result of extensive investigations to solve the above-described problems, the present inventors have found that the objects of the present invention can be attained by using a process where crude pentafluoroethane containing at least one compound selected from the group consisting of hydrofluorocarbons containing one carbon atom, hydrochlorofluorocarbons containing one carbon atom and hydrochlorocarbons containing one carbon atom is brought into contact with an adsorbent comprising a zeolite having an average pore size of 3 to 6 Å and a silica/aluminum ratio of 2.0 or less and/or a carbonaceous adsorbent having an average pore size of 3.5 to 6 Å to reduce the content of the compound contained as an impurity in the crude pentafluoroethane. The present invention has been accomplished based on this finding. The present invention provides a purification process, a production process and uses of pentafluoroethane described in the following [1] to [13].

[1] A process for purifying pentafluoroethane, comprising bringing crude pentafluoroethane containing at least one compound selected from the group consisting of hydrofluorocarbons containing one carbon atom, hydrochlorofluorocarbons containing one carbon atom and hydrochlorocarbons containing one carbon atom, into contact with an adsorbent comprising a zeolite having an average pore size of 3 to 6 Å and a silica/aluminum ratio of 2.0 or less and/or a carbonaceous adsorbent having an average pore size of 3.5 to 6 Å, to reduce the content of the compound contained as an impurity in the crude pentafluoroethane.

[2] The process as described in [1] above, wherein the hydrofluorocarbon containing one carbon atom is selected from the group consisting of fluoromethane, difluoromethane and trifluoromethane.

[3] The process as described in [1] above, wherein the hydrochlorofluorocarbon containing one carbon atom is chlorodifluoromethane.

[4] The process as described in [1] above, wherein the hydrochlorocarbon containing one carbon atom is selected from the group consisting of chloromethane, dichloromethane and trichloromethane.

[5] The process as described in any one of [1] to [4] above, wherein the total content of the compound contained as an impurity in the crude pentafluoroethane is 1 vol % or less.

[6] The process as described in any one of [1] to [5] above, wherein the crude pentafluoroethane is brought into contact with the adsorbent under a pressure of 1 MPa or less.

[7] The process as described in any one of [1] to [6] above, wherein the total content of the compound contained as an impurity in the crude pentafluoroethane is reduced to 150 vol ppm or less.

[8] The process as described in any one of [1] to [7] above, wherein the total content of hydrofluorocarbons containing one carbon atom, contained as an impurity in the crude pentafluoroethane, is reduced to 100 vol ppm or less.

[9] The process as described in any one of [1] to [8] above, wherein the total content of hydrochlorocarbons containing one carbon atom, contained as an impurity in the crude pentafluoroethane, is reduced to 50 vol ppm or less.

[10] The process as described in any one of [1] to [9] above, wherein the crude pentafluoroethane is obtained by a process comprising the following steps:

(1) a step of reacting at least one member selected from the group consisting of tetrachloroethylene, 2,2-dichloro-1,1,1-trifluoroethane and 2-chloro-1,1,1,2-tetrafluoroethane with hydrogen fluoride in the presence of a fluorination catalyst to obtain pentafluoroethane, and (2) a step of bringing pentafluoroethane obtained in step (1) into contact with hydrogen, a step of bringing pentafluoroethane obtained in step (1) into contact with oxygen and/or an oxygen-containing compound, or a step of bringing pentafluoroethane obtained in step (1) into contact with hydrogen and then into contact with oxygen and/or an oxygen-containing compound.

[11] A process for producing pentafluoroethane, comprising the following steps:

(1) a step of reacting at least one member selected from the group consisting of tetrachloroethylene, 2,2-dichloro-1,1,1-trifluoroethane and 2-chloro-1,1,1,2-tetrafluoroethane with hydrogen fluoride in the presence of a fluorination catalyst to obtain pentafluoroethane, (2) a step of bringing pentafluoroethane obtained in step (1) into contact with hydrogen, a step of bringing pentafluoroethane obtained in step (1) into contact with oxygen and/or an oxygen-containing compound, or a step of bringing pentafluoroethane obtained in step (1) into contact with hydrogen and then into contact with oxygen and/or an oxygen-containing compound, and (3) a step of purifying the pentafluoroethane obtained in step (2) by using the process described in any one of [1] to [10] above.

[12] A process for producing hexafluoroethane, comprising reacting a fluorine gas with pentafluoroethane purified by using the process described in any one of [1] to [10] above.

[13] A refrigerant comprising pentafluoroethane purified by using the process described in any one of [1] to [10] above.

BEST MODE FOR CARRYING OUT THE INVENTION

The preferred embodiments of the present invention are described below.

As described above, for the production of a pentafluoroethane, for example, a method of fluorinating tetrachloroethylene or a fluoride thereof with hydrogen fluoride (HF) in the presence of a fluorination catalyst is known.

When pentafluoroethane is produced by this method, even if a generally employed purification step such as distillation is performed, impurities which are difficult to separate from pentafluoroethane are contained in the material. Examples of the impurity include hydrofluorocarbons, hydrochlorofluorocarbons and hydrochlorocarbons. Also, even if a method of hydrogen-reducing chloropentafluoroethane in the presence of a catalyst is used, these impurities are similarly contained. Accordingly, in order to purify pentafluoroethane to a high purity, these impurities must be removed.

The process for purifying pentafluoroethane of the present invention is characterized in that crude pentafluoroethane containing at least one compound selected from the group consisting of hydrofluorocarbons containing one carbon atom, hydrochlorofluorocarbons containing one carbon atom and hydrochlorocarbons containing one carbon atom is brought into contact with an adsorbent comprising a zeolite having an average pore size of 3 to 6 Å and a silica/aluminum ratio of 2.0 or less and/or a carbonaceous adsorbent having an average pore size of 3.5 to 6 Å and thereby the content of the compound contained as an impurity in the crude pentafluoroethane is reduced.

The hydrofluorocarbon containing one carbon atom, contained as an impurity in the crude pentafluoroethane, may be at least one compound selected from the group consisting of fluoromethane, difluoromethane and trifluoromethane. The hydrochlorofluorocarbon containing one carbon atom may be chlorodifluoromethane. The hydrochlorocarbon containing one carbon atom may be at least one compound selected from the group consisting of chloromethane, dichloromethane and trichloromethane. The crude pentafluoroethane containing these impurities is difficult to purify only by a distillation operation. While taking account of the polarity and pore size of the adsorbent, the present inventors have made studies, for example, by changing the kind of adsorbent or the adsorption conditions.

As a result, it has been found that the above-described impurities can be selectively adsorbed and removed by contacting these impurities with a zeolite having an average pore size of 3 to 6 Å and a silica/aluminum ratio (Si/Al ratio) of 2.0 or less. Even when the silica/aluminum ratio is 2.0 or less, if the average pore size of the zeolite is less than 3 Å or exceeding 6 Å, the effect of reducing those impurities is not obtained. Also, even when the average pore size is in the range from 3 to 6 Å, if the silica/aluminum ratio of the zeolite exceeds 2.0, the effect of reducing the amount of the impurities is not obtained.

Furthermore, it has been found that the above-described impurities can be selectively adsorbed and removed by contacting these impurities with a carbonaceous adsorbent (molecular sieving carbon) having an average pore size of 3.5 to 6 Å. If the average pore size of the carbonaceous adsorbent used is less than 3.5 Å or exceeds 6 Å, the effect of reducing the impurities is not obtained. For example, an activated carbon having an average pore size of about 35 Å is generally used and known to have a strong adsorbing ability, however, this cannot provide an effect of reducing those impurities.

The above-described zeolite and carbonaceous adsorbent may be used individually or both may be used in combination at an arbitrary ratio.

The total content of those impurities contained as an impurity in the crude pentafluoroethane is preferably 1 vol % or less, more preferably 0.5 vol % or less. If the total content of the impurities exceeds 1 vol %, the amount of the adsorbent used increases or the equipment cost and the like disadvantageously rise.

In the process for purifying pentafluoroethane of the present invention, the method for bringing crude pentafluoroethane containing those impurities into contact with the adsorbent is not particularly limited and, for example, these may be contacted either in a gas phase or in a liquid phase. The method of contacting these in a liquid phase is efficient and preferred. For contact in a liquid phase, a known method such as batch system or continuous system can be used. For example, a method where two units of a fixed bed-system adsorption tower are provided and when one adsorption tower reaches a saturated adsorption, the unit is changed over and the regeneration is performed can be used. The pressure for bringing the crude pentafluoroethane into contact with the adsorbent is preferably 1 MPa or less. If this pressure exceeds 1 MPa, the equipment cost disadvantageously increases.

The crude pentafluoroethane is preferably obtained by a process comprising:

(1) a step of reacting at least one member selected from the group consisting of tetrachloroethylene, 2,2-dichloro-1,1,1-trifluoroethane and 2-chloro-1,1,1,2-tetrafluoroethane with hydrogen fluoride in the presence of a fluorination catalyst to obtain pentafluoroethane, and (2) a step of bringing pentafluoroethane obtained in step (1) into contact with hydrogen, a step of bringing pentafluoroethane obtained in step (1) into contact with oxygen and/or an oxygen-containing compound, or a step of bringing pentafluoroethane obtained in step (1) into contact with hydrogen and then into contact with oxygen and/or an oxygen-containing compound.

Step (1) may use a method of performing a fluorination reaction between the starting material, for example, tetrachloroethylene, and hydrogen fluoride through two stages in the presence of a fluorination catalyst to obtain pentafluoroethane. The fluorination catalyst is preferably a supported or bulk catalyst mainly comprising a trivalent chromium oxide.

In step (2), in the case of performing the step of bringing pentafluoroethane obtained in step (1) into contact with hydrogen, this may be performed in the presence of a supported catalyst where at least one member selected from the group consisting of palladium, rhodium, ruthenium, rhenium, platinum and gold is supported on a support. The reaction temperature is from 150 to 400° C. By the contact with hydrogen, a reduction and hydrogenation reaction of, for example, hydrochlorocarbons takes place.

In step (2), in the case of performing the step of bringing pentafluoroethane obtained in step (1) into contact with oxygen and/or an oxygen-containing compound, this may be performed in the presence of a supported or bulk catalyst mainly comprising a trivalent chromium oxide or in the presence of a supported catalyst where at least one member selected from the group consisting of palladium, rhodium, ruthenium, rhenium, platinum and gold is supported on a support. The reaction temperature is from 150 to 400° C. Examples of the oxygen-containing compound which can be used include nitrogen monoxide (NO), nitrous oxide ($N_2O$), nitrogen dioxide ($NO_2$) and ozone ($O_3$). By this treatment, hydrofluorocarbons contained as an impurity can be converted into $CO_2$ or the like. Step (2) is preferably performed by bringing the pentafluoroethane obtained in step (1) into contact with hydrogen and then into contact with oxygen and/or an oxygen-containing compound.

After the compound contained as an impurity in the crude pentafluoroethane is treated with the adsorbent, the total content of the compound contained in the pentafluoroethane can be reduced to 150 vol ppm or less, even to 100 vol ppm or less. Also, the total content of the hydrofluorocarbons containing one carbon atom, contained as an impurity in pentafluoroethane purified by using the purification process of the present invention, can be reduced to 100 vol ppm or less, even to 50 vol ppm or less. Furthermore, the total content of the hydrochlorocarbons containing one carbon atom can be reduced to 50 vol ppm or less, even to 30 vol ppm or less. The content of the compound contained as an impurity in pentafluoroethane can be measured by gas chromatography (GC) using TCD method or FID method, or gas chromatography-mass spectrometry (GC-MS).

The present invention also provides a process for producing pentafluoroethane, comprising the following steps:

(1) a step of reacting at least one member selected from the group consisting of tetrachloroethylene, 2,2-dichloro-1,1,1-trifluoroethane and 2-chloro-1,1,1,2-tetrafluoroethane with hydrogen fluoride in the presence of a fluorination catalyst to obtain a pentafluoroethane, (2) a step of bringing pentafluoroethane obtained in step (1) into contact with hydrogen, a step of bringing pentafluoroethane obtained in step (1) into contact with oxygen and/or an oxygen-containing compound, or a step of bringing pentafluoroethane obtained in step. (1) into contact with hydrogen and then into contact with oxygen and/or an oxygen-containing compound, and (3) a step of purifying pentafluoroethane obtained in step (2) by using the process described above.

Uses of pentafluoroethane obtained by using the purification process of the present invention are described below.

The high-purity pentafluoroethane is a substitute for chlorodifluoromethane ($CHClF_2$) which is currently used as a working fluid of cryogenic refrigerators, and this can be used as a mixed refrigerant comprising difluoromethane/pentafluoroethane/1,1,1,2-tetrafluoroethane and also as a mixed refrigerant comprising difluoromethane/pentafluoroethane.

Furthermore, the high-purity pentafluoroethane can be used as a starting material for the production of hexafluoroethane. Particularly, in the method of producing hexafluoroethane by a reaction of pentafluoroethane with a fluorine gas, when the high-purity pentafluoroethane is used as a starting material, the production of impurities which are difficult to separate from the objective hexafluoroethane can be prevented. In addition, when the high-purity pentafluoroethane is used as a starting material, the latitude in setting the fluorination reaction conditions can be broadened and, as a result, the reaction can be stably controlled and the purification step can be simplified.

The high-purity pentafluoroethane or a mixed gas thereof with an inert gas (e.g., He, $N_2$, Ar), HCl, $O_2$, $H_2$ or the like can be used as an etching gas in the etching step in the process of producing a semiconductor device. In the process of producing a semiconductor device such as an LSI, a TFT and an organic EL, a thin or thick film is formed using a CVD method, a sputtering method or a vapor deposition method and a circuit pattern is formed by etching, where a gas containing the pentafluoroethane can be used as the etching gas. The etching using pentafluoroethane can be performed under various dry etching conditions such as plasma etching and microwave etching.

The present invention is further illustrated below by referring to the following examples, however, the present invention is not limited to these examples.

PREPARATION EXAMPLE 1 OF CRUDE PENTAFLUOROETHANE

Raw Material Example 1

Tetrachloroethylene and hydrogen fluoride were introduced into a first reactor filled with a catalyst to produce a gas mainly comprising 2,2-dichloro-1,1,1-trifluoroethane and chloro-1,1,1,2-tetrafluoroethane which are intermediates. This gas was introduced together with HF into a second reactor to produce pentafluoroethane. The produced pentafluoroethane was distilled to obtain pentafluoroethane containing, as impurities, chloropentafluoroethane, fluoromethane, difluoromethane, chloromethane, chlorodifluoromethane, 1,1,1-trifluoromethane and the like. The purity of the pentafluoroethane was about 99.4 vol %. Subsequently, this pentafluoroethane was reacted with hydrogen in the presence of a commercially available hydrogenation catalyst (reaction pressure: 0.15 MPa, reaction temperature: 220° C.). The acid content contained in the product mainly comprising pentafluoroethane was removed by a known method and the residue was distilled to obtain a crude pentafluoroethane. The obtained crude pentafluoroethane was analyzed by a gas chromatograph and found to have the composition shown in Table 1.

TABLE 1

| Compound | Concentration (vol %) |
| --- | --- |
| $CF_3CHF_2$ | 99.8404 |
| $CF_3CClF_2$ | 0.0082 |
| $CF_3CH_2F$ | 0.0024 |
| $CF_3CH_3$ | 0.0879 |
| $CH_2F_2$ | 0.0482 |
| $CHF_3$ | 0.0021 |
| $CHClF_2$ | 0.0020 |
| $CH_3Cl$ | 0.0088 |

PREPARATION EXAMPLE 2 OF CRUDE PENTAFLUOROETHANE

Raw Material Example 2

The pentafluoroethane obtained in Raw Material Example 1 was introduced together with air into a reactor filled with a palladium/aluminum catalyst and reacted under such conditions that the reaction pressure was 0.2 MPa and the reaction temperature was 280° C. The acid content and carbon dioxide contained in the gas at the outlet of the reactor were partially removed by washing the gas with an aqueous potassium hydroxide solution and then the gas was distilled to obtain a crude pentafluoroethane. The obtained crude pentafluoroethane was analyzed by a gas chromatograph and found to have the composition shown in Table 2.

TABLE 2

| Compound | Concentration (vol %) |
| --- | --- |
| $CF_3CHF_2$ | 99.9522 |
| $CF_3CClF_2$ | 0.0081 |
| $CF_3CH_2F$ | 0.0018 |
| $CF_3CH_3$ | 0.0088 |
| $CH_2F_2$ | 0.0246 |
| $CHF_3$ | 0.0019 |
| $CHClF_2$ | 0.0020 |
| $CH_3Cl$ | 0.0087 |

PREPARATION EXAMPLE 3 OF CRUDE PENTAFLUOROETHANE

Raw Material Example 3

To the crude pentafluoroethane obtained in Raw Material Example 2, $CH_2F_2$ and $CH_3Cl$ were further added to prepare a crude pentafluoroethane raw material 3. This was analyzed by a gas chromatograph and found to have the composition shown in Table 3.

TABLE 3

| Compound | Concentration (vol %) |
| --- | --- |
| $CF_3CHF_2$ | 99.6322 |
| $CF_3CClF_2$ | 0.0081 |
| $CF_3CH_2F$ | 0.0018 |
| $CF_3CH_3$ | 0.0087 |
| $CH_2F_2$ | 0.2325 |
| $CHF_3$ | 0.0019 |
| $CHClF_2$ | 0.0020 |
| $CH_3Cl$ | 0.1128 |

EXAMPLE 1

A zeolite (Molecular Sieves 4A (produced by Union Showa K.K., average pore size: 3.5 Å, silica/aluminum ratio=1.0)) (20 g) was filled in a 200 ml stainless steel cylinder and vacuum dried. Thereto, about 100 g of the crude pentafluoroethane of Raw Material Example 1 was filled while cooling the cylinder and occasionally stirred while keeping the temperature at −10° C. After about 20 hours, the liquid phase part was analyzed by a gas chromatograph. The analysis results are shown in Table 4.

TABLE 4

| Compound | Concentration (vol %) |
| --- | --- |
| $CF_3CHF_2$ | 99.8979 |
| $CF_3CClF_2$ | 0.0082 |
| $CF_3CH_2F$ | 0.0021 |
| $CF_3CH_3$ | 0.0880 |
| $CH_2F_2$ | 0.0001 |
| $CHF_3$ | 0.0015 |
| $CHClF_2$ | 0.0019 |
| $CH_3Cl$ | 0.0003 |

As apparent from the analysis results shown in Table 4, $CH_2F_2$ and $CH_3Cl$ could be selectively adsorbed and removed.

EXAMPLE 2

Molecular Sieves 4A (20 g) was filled into a 200 ml stainless steel cylinder in the same manner as in Example 1 and vacuum dried. Thereto, about 100 g of the crude pentafluoroethane of Raw Material Example 2 was filled while cooling the cylinder and occasionally stirred while keeping the temperature at room temperature (20° C.). After about 20 hours, the liquid phase part was analyzed by a gas chromatograph. The analysis results are shown in Table 5.

TABLE 5

| Compound | Concentration (vol %) |
| --- | --- |
| $CF_3CHF_2$ | 99.9790 |
| $CF_3CClF_2$ | 0.0082 |
| $CF_3CH_2F$ | 0.0017 |
| $CF_3CH_3$ | 0.0087 |
| $CH_2F_2$ | 0.0001 |
| $CHF_3$ | 0.0009 |
| $CHClF_2$ | 0.0012 |
| $CH_3Cl$ | 0.0002 |

As apparent from the analysis results shown in Table 5, a high-purity pentafluoroethane having a purity of 99.97 vol % or more was obtained.

EXAMPLE 3

Molecular Sieves 4A (30 g) was filled into a 200 ml stainless steel cylinder in the same manner as in Example 1. Thereto, about 100 g of the crude pentafluoroethane of Raw Material Example 3 was filled while cooling the cylinder, vacuum-dried and then occasionally stirred while keeping the temperature at room temperature (25° C.). After about 20 hours, the liquid phase part was analyzed by a gas chromatograph. The analysis results are shown in Table 6.

TABLE 6

| Compound | Concentration (vol %) |
|---|---|
| $CF_3CHF_2$ | 99.9789 |
| $CF_3CClF_2$ | 0.0082 |
| $CF_3CH_2F$ | 0.0016 |
| $CF_3CH_3$ | 0.0087 |
| $CH_2F_2$ | 0.0011 |
| $CHF_3$ | 0.0006 |
| $CHClF_2$ | 0.0008 |
| $CH_3Cl$ | 0.0001 |

EXAMPLE 4

A carbonaceous adsorbent (Molecular Sieving Carbon, produced by Takeda Chemical Industries, Ltd., average pore size: 4 Å) (20 g) was filled into a 200 ml stainless steel cylinder and vacuum dried. Thereto, about 100 g of the crude pentafluoroethane of Raw Material Example 1 was filled while cooling the cylinder and occasionally stirred while keeping the temperature at −20° C. After about 20 hours, the liquid phase part was analyzed by a gas chromatograph. The analysis results are shown in Table 7.

TABLE 7

| Compound | Concentration (vol %) |
|---|---|
| $CF_3CHF_2$ | 99.8992 |
| $CF_3CClF_2$ | 0.0082 |
| $CF_3CH_2F$ | 0.0023 |
| $CF_3CH_3$ | 0.0880 |
| $CH_2F_2$ | 0.0003 |
| $CHF_3$ | 0.0006 |
| $CHClF_2$ | 0.0012 |
| $CH_3Cl$ | 0.0002 |

As apparent from the analysis results shown in Table 7, $CH_2F_2$ and $CH_3Cl$ could be selectively adsorbed and removed.

EXAMPLE 5

Molecular Sieves 4A (15 g) used in Example 1 and 15 g of Molecular Sieving Carbon used in Example 4 were mixed and filled into a 200 ml stainless steel cylinder and vacuum dried. Thereto, about 100 g of the crude pentafluoroethane of Raw Material Example 3 was filled while cooling the cylinder and occasionally stirred while keeping the temperature at room temperature (25° C.). After about 20 hours, the liquid phase part was analyzed by a gas chromatograph. The analysis results are shown in Table 8.

TABLE 8

| Compound | Concentration (vol %) |
|---|---|
| $CF_3CHF_2$ | 99.9786 |
| $CF_3CClF_2$ | 0.0082 |
| $CF_3CH_2F$ | 0.0017 |
| $CF_3CH_3$ | 0.0088 |
| $CH_2F_2$ | 0.0004 |
| $CHF_3$ | 0.0007 |
| $CHClF_2$ | 0.0013 |
| $CH_3Cl$ | 0.0003 |

COMPARATIVE EXAMPLE 1

A zeolite (Molecular Sieves 13X (produced by Union Showa K.K., average pore size: 10 Å, silica/aluminum ratio=1.2)) (20 g) was filled in a 200 ml stainless steel cylinder and vacuum dried. Thereto, about 100 g of the crude pentafluoroethane of Raw Material Example 2 was filled while cooling the cylinder and occasionally stirred while keeping the temperature at room temperature (25° C.). After about 20 hours, the liquid phase part was analyzed by a gas chromatograph. The analysis results are shown in Table 9.

TABLE 9

| Compound | Concentration (vol %) |
|---|---|
| $CF_3CHF_2$ | 99.9452 |
| $CF_3CClF_2$ | 0.0082 |
| $CF_3CH_2F$ | 0.0002 |
| $CF_3CH_3$ | 0.0090 |
| $CH_2F_2$ | 0.0251 |
| $CHF_3$ | 0.0012 |
| $CHClF_2$ | 0.0021 |
| $CH_3Cl$ | 0.0090 |

As apparent from the analysis results shown in Table 9, even when the silica/aluminum ratio is 2.0 or less, if the average pore size exceeds 6 Å, the selective adsorption and removal cannot be attained.

COMPARATIVE EXAMPLE 2

An activated carbon (granular Shirosagi KL (produced by Takeda Chemical Industries, Ltd., average pore size: 35 Å)) (20 g) was filled in a 200 ml stainless steel cylinder and vacuum dried. Thereto, about 100 g of the crude pentafluoroethane of Raw Material Example 2 was filled while cooling the cylinder and occasionally stirred while keeping the temperature at room temperature (25° C.). After about 20 hours, the liquid phase part was analyzed by a gas chromatograph. Similarly to Comparative Example 1, the selective adsorption and removal could not be attained and the reduction in the content of $CH_2F_2$ or $CH_3Cl$ was not attained.

COMPARATIVE EXAMPLE 3

The purification was performed by the same operation under the same conditions as in Comparative Example 1 except for filling a zeolite (H-ZSM-5 (produced by N.E. Chemcat Corporation, average pore size: 6 Å, silica/aluminum ratio 15)) into the 200 ml stainless steel cylinder. As a result of analysis, the reduction in the content of $CH_2F_2$ or $CH_3Cl$ was not confirmed.

INDUSTRIAL APPLICABILITY

As described in the foregoing pages, when the purification process of the present invention is used, high-purity pentafluoroethane can be obtained. Pentafluoroethane obtained according to the present invention can be used as a low temperature refrigerant or a starting material for the production of high-purity hexafluoroethane.

The invention claimed is:

1. A process for purifying pentafluoroethane, comprising bringing crude pentafluoroethane containing at least one compound selected from the group consisting of hydrofluorocarbons containing one carbon atom, hydrochlorofluorocarbons containing one carbon atom and hydrochlorocarbons containing one carbon atom, into contact with an adsorbent comprising a zeolite having an average pore size of 3 to 6 Å and a silica/aluminum ratio of 2.0 or less and/or a carbonaceous adsorbent having an average pore size of 3.5 to 6 Å, to reduce the content of said compound contained as an impurity in the crude pentafluoroethane.

2. The process as claimed in claim 1, wherein said hydrofluorocarbon containing one carbon atom is selected from the group consisting of fluoromethane, difluoromethane and trifluoromethane.

3. The process as claimed in claim 1, wherein said hydrochlorofluorocarbon containing one carbon atom is chlorodifluoromethane.

4. The process as claimed in claim 1, wherein said hydrochlorocarbon containing one carbon atom is selected from the group consisting of chloromethane, dichloromethane and trichloromethane.

5. The process as claimed in any one of claims 1 to 4, wherein the total content of said compound contained as an impurity in the crude pentafluoroethane is 1 vol % or less.

6. The process as claimed in claim 1, wherein the crude pentafluoroethane is brought into contact with said adsorbent under a pressure of 1 MPa or less.

7. The process as claimed in claim 1, wherein the total content of said compound contained as an impurity in the crude pentafluoroethane is reduced to 150 vol ppm or less.

8. The process as claimed in claim 1, wherein the total content of hydrofluorocarbons containing one carbon atom, contained as an impurity in the crude pentafluoroethane, is reduced to 100 vol ppm or less.

9. The process as claimed in claim 1, wherein the total content of hydrochlorocarbons containing one carbon atom, contained as an impurity in the crude pentafluoroethane, is reduced to 50 vol ppm or less.

10. A process for purifying pentafluoroethane, comprising
bringing crude pentafluoroethane containing at least one compound selected from the group consisting of hydrofluorocarbons containing one carbon atom, hydrochlorofluorocarbons containing one carbon atom and hydrochlorocarbons containing one carbon atom, into contact with an adsorbent comprising a zeolite having an average pore size of 3 to 6 Å and a silica/aluminum ratio of 2.0 or less and/or a carbonaceous adsorbent having an average pore size of 3.5 to 6 Å, to reduce the content of said compound contained as an impurity in the crude pentafluoroethane, wherein the crude pentafluoroethane is obtained by a process comprising the following steps:

(1) a step of reacting at least one member selected from the group consisting of tetrachloroethylene, 2,2-dichloro-1,1,1-trifluoroethane and 2-chloro-1,1,1,2-tetrafluoroethane with hydrogen fluoride in the presence of a fluorination catalyst to obtain pentafluoroethane, and (2) a step of bringing pentafluoroethane obtained in step (1) into contact with hydrogen, a step of bringing pentafluoroethane obtained in step (1) into contact with oxygen and/or an oxygen-containing compound, or a step of bringing pentafluoroethane obtained in step (1) into contact with hydrogen and then into contact with oxygen and/or an oxygen-containing compound.

11. A process for producing pentafluoroethane, comprising the following steps:

(1) a step of reacting at least one member selected from the group consisting of tetrachloroethylene, 2,2-dichloro-1,1,1-trifluoroethane and 2-chloro-1,1,1,2-tetrafluoroethane with hydrogen fluoride in the presence of a fluorination catalyst to obtain pentafluoroethane, (2) a step of bringing pentafluoroethane obtained in step (1) into contact with hydrogen, a step of bringing pentafluoroethane obtained in step (1) into contact with oxygen and/or an oxygen-containing compound, or a step of bringing pentafluoroethane obtained in step (1) into contact with hydrogen and then into contact with oxygen and/or an oxygen-containing compound, and (3) a step of purifying pentafluoroethane obtained in step (2) comprising bringing crude pentafluoroethane containing at least one compound selected from the group consisting of hydrofluorocarbons containing one carbon atom, hydrochlorofluorocarbons containing one carbon atom and hydrochlorocarbons containing one carbon atom, into contact with an adsorbent comprising a zeolite having an average pore size of 3 to 6 Å and a silica/aluminum ratio of 2.0 or less and/or a carbonaceous adsorbent having an average pore size of 3.5 to 6 Å, to reduce the content of said compound contained as an impurity in the crude pentafluoroethane.

12. A process for producing hexafluoroethane, comprising reacting a fluorine gas with pentafluoroethane purified by using the process claimed in claim 1.

* * * * *